United States Patent [19]

Hammer et al.

[11] Patent Number: 5,159,063

[45] Date of Patent: Oct. 27, 1992

[54] ISOLATION AND CHARACTERIZATION OF A 120 KDA GLYCOPROTEIN PLASMA

[75] Inventors: Carl H. Hammer, Gaithersburg; Ruth M. Jacobs; Michael M. Frank, both of Bethesda, all of Md.

[73] Assignee: The United States of America as represented by the Department of Health and Human Services, Washington, D.C.

[21] Appl. No.: 305,458

[22] Filed: Feb. 2, 1989

[51] Int. Cl.$^5$ .................. C07K 15/14; A61K 35/16
[52] U.S. Cl. .................. 530/380; 530/395; 530/829; 530/830; 514/8
[58] Field of Search .................. 530/380, 830, 395; 514/8; 424/88

[56] References Cited

U.S. PATENT DOCUMENTS 4,245,051  1/1981  Reich .................. 435/212
4,339,441  7/1982  Kalman .................. 424/173

OTHER PUBLICATIONS

Ross, G. D. *Immunobiology of the Complement System*, Academic Press, Inc. New York 1986.
Eldering, E. et al. J. Biol. Chem 263(24):11776-9 Aug. 25, 1988 "Expression of Functional Human C1-".
Hammer, C. H. et al., J. Biol. Chem 264(4):2283-91 Feb. 1989, "Isolation and Characterization . . . ".
Kristensen, T. et al. FASEB Proc. 46(7):2463-69, "The Superfamily of C3b/C4b-binding Proteins", May, 1987.
Basic and Clinical Immunology, Fundenberg, H. H. et al. (editors), see p. 87, Lange Publications, 1980.
Abstract: Hammer, C. H. Jacobs, R. M., Brickman, C. M. and M. M. Frank, A New Human Complement Protein which Co-isolates with C2 (1987), Complement 4:165 (#111).

Primary Examiner—Christine Nucker
Assistant Examiner—Thomas Cunningham
Attorney, Agent, or Firm—Cushman, Darby & Cushman

[57] ABSTRACT

A substantially pure, single chain plasma protein of approximately 120 kDa having an N-terminal amino acid sequence EKNGIDIYSLTD, and a mixture of protein fragments having vasodilatory activity which fragments are generated by activated Kallikrein cleavage of the 120 kDa protein.

2 Claims, 9 Drawing Sheets

FIG. 10 a = Serum (LF)   b = NPGB/EDTA Serum (LF)
c = Serum (EB)   d = NPGB/EDTA Serum (EB)

FIG. II

ISOLATION AND CHARACTERIZATION OF A 120 KDA GLYCOPROTEIN PLASMA

BACKGROUND OF THE INVENTION

C4 is a 200 kDa three-chain glycoprotein which is present in plasma at a concentration of about 350 µg/ml, and which functions as the second complement protein in the classical complement pathway activation sequence.

The binding of an appropriate antibody to a substrate leads to binding and activation of the complex complement protein C1. Activated C1 in turn cleaves a 9 kDa fragment, C4a, from the N-terminal of the C4 alpha chain thereby exposing an internal thio ester which links amino acids at positions 991 and 994 within the C4d region of the C4 alpha' subunit. Upon exposure, this highly reactive group undergoes nucleophilic attack thereby forming a covalent bond with the target substrate.

The major fragment of C4, C4b, is covalently bound to the target substrate following cleavage and release of C4a, and acts as a receptor for C2 of the classical pathway. C2 binds to C4b and is cleaved in turn, by active C1 to continue the complement cascade.

Several proteins in addition to C2 have been identified which bind to C4b. For instance, the C4-binding protein C4-bp, has been found to bind to fluid phase C4b, as well as to C4b which is deposited on a target surface. C4-bp facilitates the cleavage and degradation of C4b which, when cell bound, is cleaved as part of the degradation pathway following association with factor I.

At least two cell membrane-bound proteins also bind to C4b. These proteins include CR1 (the C3b/C4b complement receptor) and gp45-70 which is believed to participate in the degradation of C3b and C4b on cells lacking CR1.

A third cell membrane associated protein also exists which has been designated DAF, decay-accelerating factor. DAF is found on a wide variety of cell types and is a potent inhibitor of C3 convertase of the classical complement pathway and, to a lesser extent, of the alternative complement pathway as well. It is unknown whether this 70 kDa, single chain glycoprotein interacts with C4b/C3b or the enzymatic units C2a or Bb of the C3 convertases.

SUMMARY OF INVENTION

The present inventors disclose herein a previously unknown, substantially pure, single chain, plasma protein of approximately 120 kDa (hereinafter, "the 120 kDa protein") one form of which binds to activated C4 and C3 of the classical complement pathway and which inhibits lytic functional activity of the pathway at multiple steps (including but not limited to C1, C4, C2 and C3 site formation). Quantitative Mancini analysis has identified about 300 µg/ml of this protein in plasma and serum.

Protein analysis shows that the molecule contains approximately equal amounts of N and O-linked carbohydrates of 15% each. The protein is cleaved specifically by activated Kallikrein of the contact system into fragments of 85 and 35 kDa; the 85 kDa fragment is subsequently cleaved into fragments of 60 and 25 kDa. Studies on the intact and fragmented protein reveal that a mixture of the fragments, but not the intact protein molecule, has potent vasodilating activity when injected into normal guinea pigs.

The N-terminal amino acid sequence in the intact protein has been determined to be: EKNGIDIYSLTVD. This confirms its identity as a unique protein with homology to the human LDL receptor (EGF domain).

Experiments designed to delineate a functional role for the 120 kDa protein have demonstrated a consistent inhibition of C1 site generation on EAC4b which inhibition is dose dependent and reversible. Thus, the disclosed protein appears to be a new complement regulatory factor. This belief is supported by the fact that the 120 kDa protein shares many physiochemical characteristics with the C2 protein of the classical complement pathway. For example, both proteins are single chain molecules of similar molecular weight (120 kDa versus 95 kDa) as determined by sodium dodecyl sulfate-gel electrophoresis (SDS-PAGE) in the presence or absence of a reducing agent; they co-precipitate on polyethylene glycol (PEG) fractionation; they share common antigenic domains (as shown by Western Blot analysis); they radioiodinate to a similar extent using two different methods of iodination; and they specifically bind to iC4/C4b-Sepharose.

There is further evidence, however, which clarifies that the 120 kDa and the C2 proteins are separate and unique entities. The evidence supporting this conclusion includes the lack of C2 functional activity by the 120 kDa protein; a serum concentration of the 120 kDa protein 15× higher than that of C2; a lack of cross-immunoprecipitation between the two proteins using monospecific polyclonal antisera under standard gel techniques; different molecular weights; and different fragmentation patterns. Additionally, the 120 kDa protein is not cleaved when serum complement is activated, as is C2, and it is present in normal concentrations in genetically C2 deficient individuals.

While it is possible that the 120 kDa protein is a precursor of C2 (C3, C4 and C5 precursor molecules being known), this appears unlikely. In fact, the data indicates that the 120 kDa protein is a distinct plasma component, not an "immature" form of C2. For instance, the 120 kDa protein is present in plasma at 15× the concentration of C2 (Table II); in comparison, precursor forms C3, C4, and C5 are present at only about 1/20th the concentration of the active components.

Figure 8:
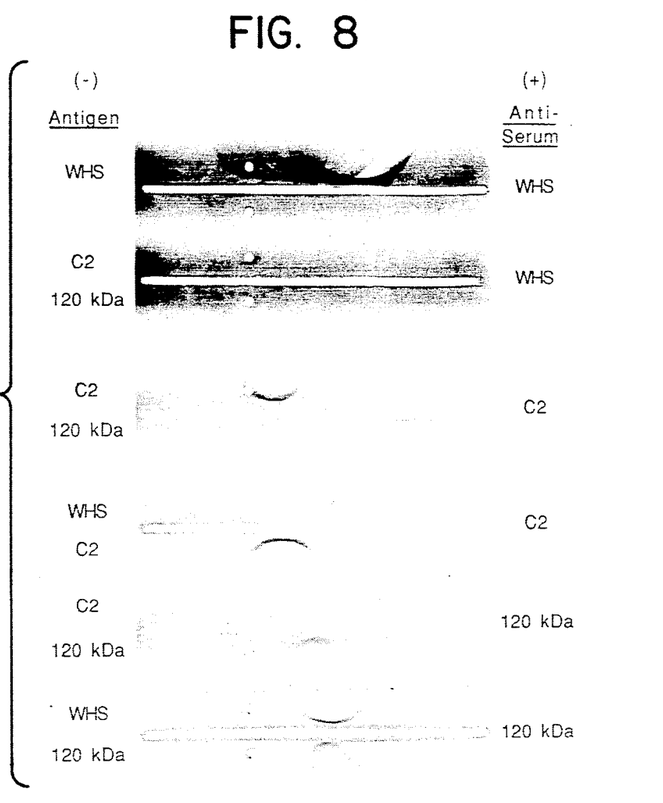
FIG. 8. IEP (immunoelectrophoresis) analysis of purified and fresh serum containing the 120 kDa protein and rabbit anti-120 kDa serum.

Additionally, it also appears unlikely that the 120 kDa protein represents a non-functional variant of the C2 molecule because precipitating antibody to C2 does not immunoprecipitate the 120 kDa protein nor vice versa (FIG. 8). This suggests that no major and/or multiple determinant sites are shared in common between the C2 and the 120 kDa proteins.

Finally, the hypotheses that the 120 kDa protein is a C2 precursor or a C2 variant are discounted by the facts that (1) the 120 kDa protein is present in C2 deficient individuals, and (2) the 120 kDa protein is not cleaved when complement is activated.

In view of the above, the novelty of the 120 kDa protein is evidenced by the fact that standard tables of plasma proteins do not cite a protein having the physiochemical properties of the disclosed 120 kDa protein (see e.g., Putnam, F. W., *The Plasma proteins. Structure, Function and Genetic Control.* Vols. 1–5. Academic Press, NY, N.Y. (1975) and Lentner, C. (ed.) *Geigy Scientific Tables.* 3:135–162 Ciba-Geigy Limited, Basle (1984)).

In addition to disclosing the 120 kDa protein, the present application also discloses a method whereby this protease sensitive, plasma protein can be isolated, substantially purified and identified for use.

It is to be understood that this general description of the invention as well as the following detailed description and drawings are exemplary and explanatory only, and are not to be viewed as restrictive of the invention.

DESCRIPTION OF THE DRAWINGS

FIG. 11. Requirement for Sepharose-bound iC4/C4b in the isolation of the 120 kDa and the C2 proteins.

Table I. Summary of purified 120 kDa protein yield—step-by-step analysis.

Table II. Functional purity of the 120 kDa protein following DEAE-Sephacel chromatography.

DETAILED DESCRIPTION OF THE INVENTION

Reference will now be made in detail to the presently preferred embodiments of the invention. Unless otherwise specified, all references cited below are to be specifically incorporated into the specification by reference.

A newly developed procedure for isolating human C2 protein was advantageously used to isolate and substantially purify a previously unidentified, unknown plasma protein of 120,000 molecular weight.

In order to purify the C2 protein, the present inventors initially used an affinity step following crude fractionation and then varied forms of ion-exchange chromatography. However, when using this procedure they noted that the low ionic strength of the elution buffer for the subsequent anion-exchange step was detrimental to C2 stability. Therefore, the present inventors performed the affinity step of the protocol prior to the DEAE-Sephacel chromatography. This resulted in the unexpected co-isolation of not one but two relatively pure proteins, C2 and the 120 kDa protein. The 120 kDa plasma protein was found to be physiochemically similar to C2, but was also noted to possess many distinct features as well.

Figure 1:
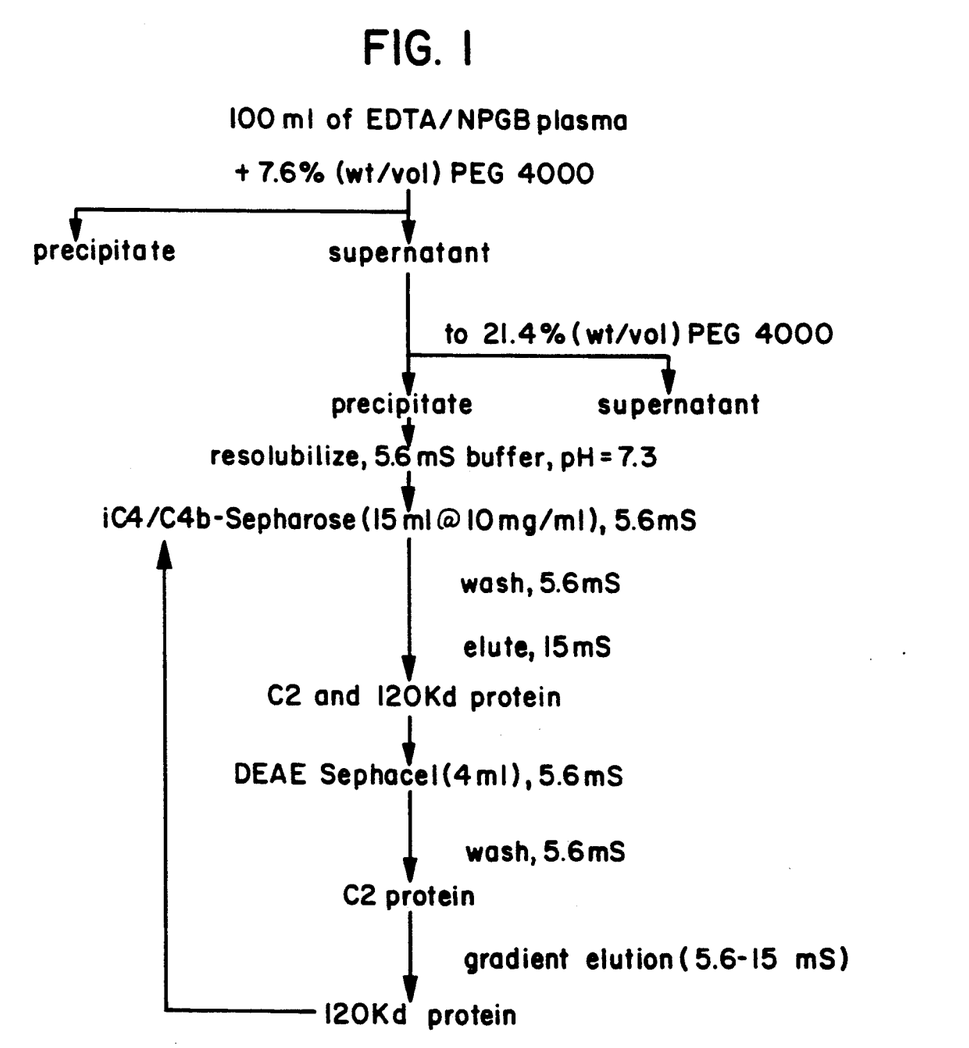
FIG. 1. Purification scheme for the isolation of the 120 kDa and C2 proteins.

Using the process disclosed herein and depicted in FIG. 1, the isolation and purification of the 120 kDa protein yields approximately 1 mg of substantially pure 120 kDa protein. Key to the success of this protocol is the use of the affinity adsorbent iC4/C4b-Sepharose (Mayer et al., J. Immunol. 105:327-341 (1970)).

MATERIALS AND METHODS

A. Analytical Procedures

1. Complement hemolytic assays a. Buffers—The following buffers were used for functional assays: isotonic Veronal-buffered saline (VBS), pH 7.4, prepared as described by Kabat and Mayer (Experimental Immunochemistry at p. 150, Charles C. Thomas, Springfield, Ill. (1964)); VBS containing 0.1% gelatin, 0.15 mM CaCl$_2$, and 1.0 mM MgCl$_2$ (GVBSM); VBS diluted to 40% with 5% dextrose solution and containing 0.1% gelatin, 0.15 mM CaCl$_2$, 1.0 mM MgCl$_2$ and 0.06M NaC$_l$ (DGVBSM); isotonic VBS containing 0.02M EDTA prepared by mixing eight parts of GVBS and two parts of 0.1M EDTA, pH 7.4 (EDTA-GVBS).

b. Complement components—The human complement (C) components C2, C3, C4, C5, C6, and C7 used in the functional reagents for the titration of the individual proteins were prepared as described by Hammer et al. (J. Biol. Chem. 256:3995-4006 (19 ), and Hammer et al., The Complement System at pp. 5-44 (Rother and Till, eds), Springer Verlag, Heidelberg (1988)). Guinea pig C1, C8 and C9 were purified as described by Nelson et al. (Immunochemistry 3:111-135 (1966); Hammer et al., Proc. Nat. Acad. Sci. U.S.A. 72:5076-5080 (1975); and Tamura and Shimada, Immunology 20:4415-425 (1971), respectively), for use in the functional reagents.

c. Assay procedures—For general component assays, sheep erythrocytes (E) were sensitized with anti-Forssman antibody (A) and converted to EAC1,4b (Rothman et al., J. Immunol 115:1312-1315 (1975)) by incubation with 500 and 200 units/ml of guinea pig C1 and human C4, respectively.

Titers for the individual C components C1 through C9 are expressed herein as the average of the product Z×reciprocal dilution obtained from three or more experimental points in the linear portion of the dose-response curve, generally below Z=1 and where Z=$-\ln(1-y)$, y=fraction of cells lysed.

Human C1 was assayed according to Gaither and Frank (Complement in Clinical Diagnosis and Management by Laboratory Methods, Todd, Sanford, and Davidson, eds., pp. 1253-1260 (1984), W. B. Saunders Co., Philadelphia, Pa.) using EAC4b (1.5×10V/ml).

Human C2 was titered in a system containing 0.1 ml of indicator cells and 0.1 ml sample dilution at 30° C. for the T-max (generally four minutes), followed by the addition of 1 ml of C-EDTA (serving as a source of C3-9) on ice with incubation for one hour at 37° C.

C-EDTA was prepared by dilution of guinea pig serum twenty-five fold in EDTA-GVBS buffer with incubation at 37° C. for 15 minutes to chelate metals therein.

Human C3, C5, C6, and C7 were titered using EAC1,4b as described for guinea pig C7 (see e.g., Hammer et al., J. Immunol. 119:1-8 (1977)). One unit/ml corresponds to 1.5×10V effective molecules in a system containing 0.1 ml of indicator cells (1.5×10V/ml), 0.2 ml of sample dilution and 0.2 ml of converting reagent. Human C8 and C9 were titrated using EAC7 and the appropriate guinea pig terminal components as described by Hammer et al. (J. Immunol., supra). Human C4 was assayed by the method of Gaither et al. (J.

Immunol. 113:574–583 (1974)) and C1 inhibitor was assayed by the method of Gigli et al. (J. Immunol. 100:1154–1164 (1968)).

Kinetic and dose experiments were performed to assess the effect of the 120 kDa protein incubation with EAC4b at 30° C. on subsequent C1 site formation. Cells treated with the 120 kDa protein for the times and concentrations indicated as well as untreated cells serving as a control were incubated with C1 at a concentration of one to two units/ml to form one to two sites/cell. The assay was performed essentially as described above (Gaither and Frank, Complement in Clinical Diagnosis and Management by Laboratory Methods, supra). EAC4b treated with the 120 kDa protein that received no C1 showed the same low level of background lysis as the untreated EAC4b.

2. Gel electrophoresis and analysis a. SDS-PAGE—The composition and purity of crude and purified protein preparations were examined by SDS-PAGE on discontinuous mini-slab gels as described by Maizel (Methods in Virology 5:179–246 (1971)). The monomer acrylamide concentration of the gel was 8.0% with an acrylamide/bisacrylamide ratio of 37.5:1. Samples were prepared and run concurrently under both reducing (2% mercaptoethanol) and non-reducing conditions against high molecular weight standards. The gels were stained for protein using 0.25% Coomassie Blue R-250 for 30 minutes.

In some experiments (where indicated) alkaline gels lacking SDS were run. Such gels were also used to obtain detergent free protein for use as an immunogen.

All reagents, standards and the mini-gel unit for SDS-PAGE were obtained from Bio-Rad Laboratories, Richmond, Calif.

b. Protein blotting—The electrophoretic transfer of proteins from SDS-PAGE slab gels to nitrocellulose was performed in a mini-gel unit by standard procedures (Towbin et al., Proc. Natl. Acad. Sci. U.S.A. 76:4350–4354 (1979)); usually for one hour on ice at 100 volts (constant) and about 300–400 mA. Pre-stained molecular weight standards (BRL, Bethesda, Md. or Bio-Rad Laboratories) were used to determine the molecular size of the blotted proteins.

c. Autoradiographic analysis—Slab gels were prepared for autoradiography by drying at 80° C. for two hours. Radioiodinated proteins in the gels were visualized by exposing the dried gels to Kodak X-Omat AR X-ray film with the use of Quanta III intensifying screens (Dupont Co., Wilmington, Del.) at −80° C.

3. Immunoelectrophoresis (IEP)—IEP analysis of proteins and antisera was performed (Weeke, Scand. J. Immunol. Suppl. 1(2):15–35 (1973)) on 3×5 inch plastic film sections of Gel-bond film (FMC Corp., Rockland, Me.) containing 1% low mp agarose (Bio-Rad Laboratories). The gel was prepared in 60 mM sodium Veronal buffer, pH 8.6, containing 50 mM NaCl, 10 mM EDTA and 5 mM NaN$_3$. The gel was washed in hypertonic salt solution, pressed and air dried following which the electrophoretic patterns were developed by staining with Crowle stain (Crowle and Cline, J. Immunol. Meth. 17:379–381 (1977)).

4. BCA protein assay

Protein was assayed by the Bicinchoninic acid (BCA) method (Smith et al., Anal. Biochem. 150:76–85 (1985)) for micro volumes as described by the manufacturer (Pierce Chemical Co., Rockford, Ill.). Bovine serum albumin (BSA, Sigma Chemical Co., St. Louis, Mo.) was used as a reference standard.

5. Single and double radial immunodiffusion

Antigenic levels of the 120 kDa protein were estimated using polyclonal monospecific antibody prepared in a rabbit by the single radial diffusion method of Mancini et al. (Immunochemistry 2:235–254 (1965)).

Double radial immunodiffusion analyses of column fractions were performed on plates prepared as above using 1% agarose in 0.05M phosphate buffered saline containing 10 mM EDTA and 0.05% sodium azide.

B. Antisera to purified proteins

For analytical purposes, small volumes of select monospecific antisera to human proteins were obtained from the following suppliers: goat anti-factor B, C1r, ceruloplasmin and C-reactive protein (Atlantic Antibodies, Scarborough, Me.); rabbit anti-haptoglobin (Boehringer Manheim Biochemicals, Indianapolis, Ind.); rabbit anti-C4-bp, alpha$_1$ lipoprotein, alpha$_2$ macroglobulin, alpha$_2$ HS glycoprotein, apolipoprotein B and hemopexin (Calbiochem-Behring, San Diego, Calif.); goat anti-IgA and rabbit anti-WHS (Cappel Laboratories, Malvern, Pa.); goat anti-C6, C7 and factor I (Genzyme, Boston, Mass.); goat anti-IgG (Meloy Laboratories, Inc., Springfield, Va.); Goat anti-HWM kininogen and sheep anti-C2 (Miles Laboratories, Inc., Naperville, Ill.) and sheep anti-inter alpha trypsin inhibitor (Sera-Tec Biochemicals, New Brunswick, N.J.).

Antisera to purified C2, C1 esterase inhibitor (C1EI), fibronectin and factor H were prepared by immunization of goats, and to C4 by immunization of a burro. Immunizations were performed with 50 to 100 μg amounts of purified protein emulsified in 50% complete Freund's adjuvant.

Immunization of a goat with pure 120 kDa protein was unsuccessful with an accumulative dose of 250 μg of antigen. A total of two ml of emulsion was given by intradermal injections at sites along the animal's back as well as at intramuscular sites in the thigh. Booster injections were given at two to three week intervals.

Successful immunization using the 120 kDa protein was accomplished in a rabbit. The rabbits were immunized in a fashion similar to that noted above using the 120 kDa protein as well as pure C2 and factor B. Although the 120 kDa protein was assessed to be pure by IEP and SDS-PAGE, it was adsorbed with Sepharose-bound IgG anti-C2, factor B, IgA, IgG, C3, factor H and C1EI prior to use as an immunogen. Likewise, pure C2 was treated with the same adsorbent lacking IgG anti-C2.

C. Antisera fractionation, immuno- and affinity-adsorbent preparation

The fractionation of antisera and immune plasma was performed using the octanoic acid procedure (Steinbuch and Audran, Arch. Biochem. Biophys. 134:279–284 (1969)) with minor modifications. Highly purified IgG was coupled to CNBr activated sepharose 4B (Pharmacia Fine Chemicals, Piscataway, N.J.) at 10 mg/ml overnight at 4° C. by the method of March et al. (Anal. Biochem. 60:149–152 (1974)). Following coupling, the unreacted groups were blocked using a solution of 0.1M ethanolamine, pH 9, at room temperature for two hours.

The affinity adsorbents iC4/C4b-Sepharose and HSA-Sepharose were prepared as above for IgG-Sepharose. In this instance, however, highly purified C4 from a large scale complement preparation (Hammer et al., J. Biol. Chem., supra and The Complement System, supra) not depleted of trace amounts of C1s, and allowed to "age" at 4° C. for at least one month, was coupled to high purity HSA (Sigma Chemical Co.) at 10 mg/ml and 6 mg/ml, respectively.

D. Radioiodination of purified proteins

Homogeneous C2 and 120 kDa proteins were each labeled with $^{125}$I using Bolton-Hunter reagent (New England Nuclear Corp., North Billerica, Mass.) as described by Lawley et al. (J. Immunol. 123:1382–1387 (1979)) or with Iodobeads (Pierce Chemical Co.). Iodinated proteins were stored frozen at $-80°$ C. in the presence of highly purified 5% BSA previously treated with p-nitrophenyl-p'-guanidino benzoate (NPGB) at 25 $\mu$M.

E. Purification procedure

The purification protocol for the isolation and purification of the 120 kDa plasma protein comprises the steps of:

a) mixing fresh anti-coagulated whole blood with EDTA, NPGB and SBTI;

b) precipitating the protein from said plasma in 7.6% to 21.6% (wt/vol) PEG;

c) collecting the precipitated protein by centrifugation;

d) immediately solubilizing the precipitated protein in GVBM, about 5.6 mS, with NPGB;

e) immediately applying the solubilized protein on an iC4/C4b-Sepharose affinity column equilibrated in GVBSM, about 6 mS, and washed with about 10 column volumes of equilibration buffer;

f) eluting the protein from the column with about four column volumes of GVBS, about 15.2 mS;

g) pooling the eluate and diluting the eluate with GVB buffer, about 0.5 mS, to yield about 5.6 mS;

h) applying the eluate to a DEAE-Sephacel column equilibrated with GVBS, about 5.6 mS, and washing the column with about two column volumes of equilibration buffer;

i) recovering the 120 kDa protein from the column with a linear salt gradient of 40 ml to about 15 mS;

j) diluting the 120 kDa protein to about 5.6 mS with GVBM, about 0.5 mS, applying the diluted protein on an iC4/C4b-Sepharose column equilibrated with GVBSM, about 5.6 mS and washing the column with an approximately 5.6 mS buffer prior to step elution with GVBS at about 15 mS in order to remove trace contaminants and to effect final protein purification.

The protocol was originally optimized for C2 recovery, but surprisingly resulted in the co-isolation of the 120 kDa protein as well (FIG. 1). Resolution of the two proteins on DEAE-Sephacel is obtained by careful selection of specific elution conditions.

Figure 2:
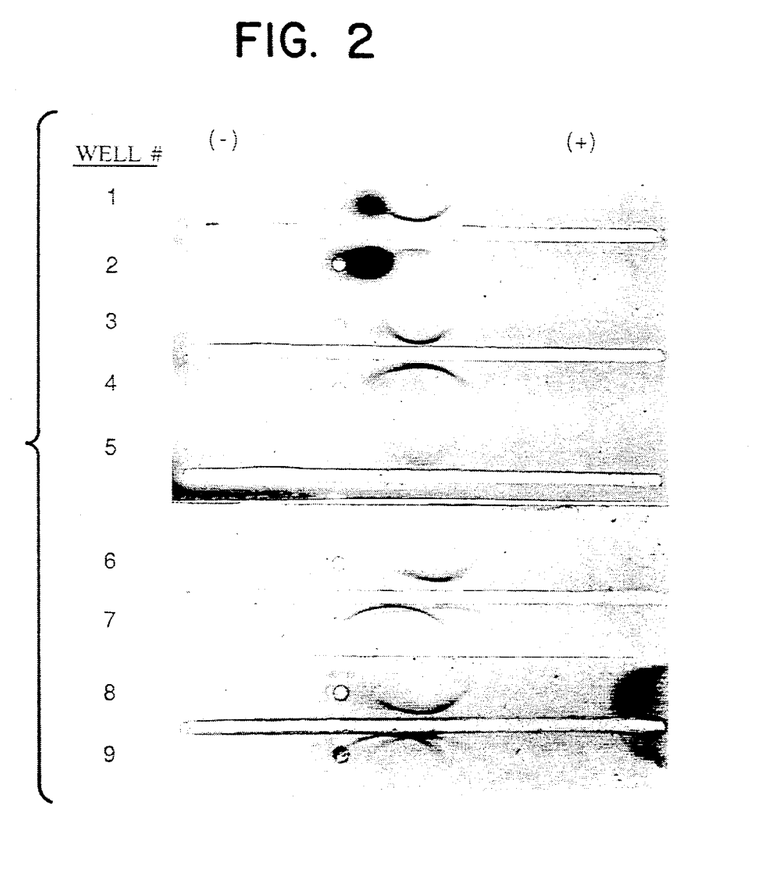
FIG. 2. IEP analysis of the 120 kDa protein during purification and storage.
Figure 2:
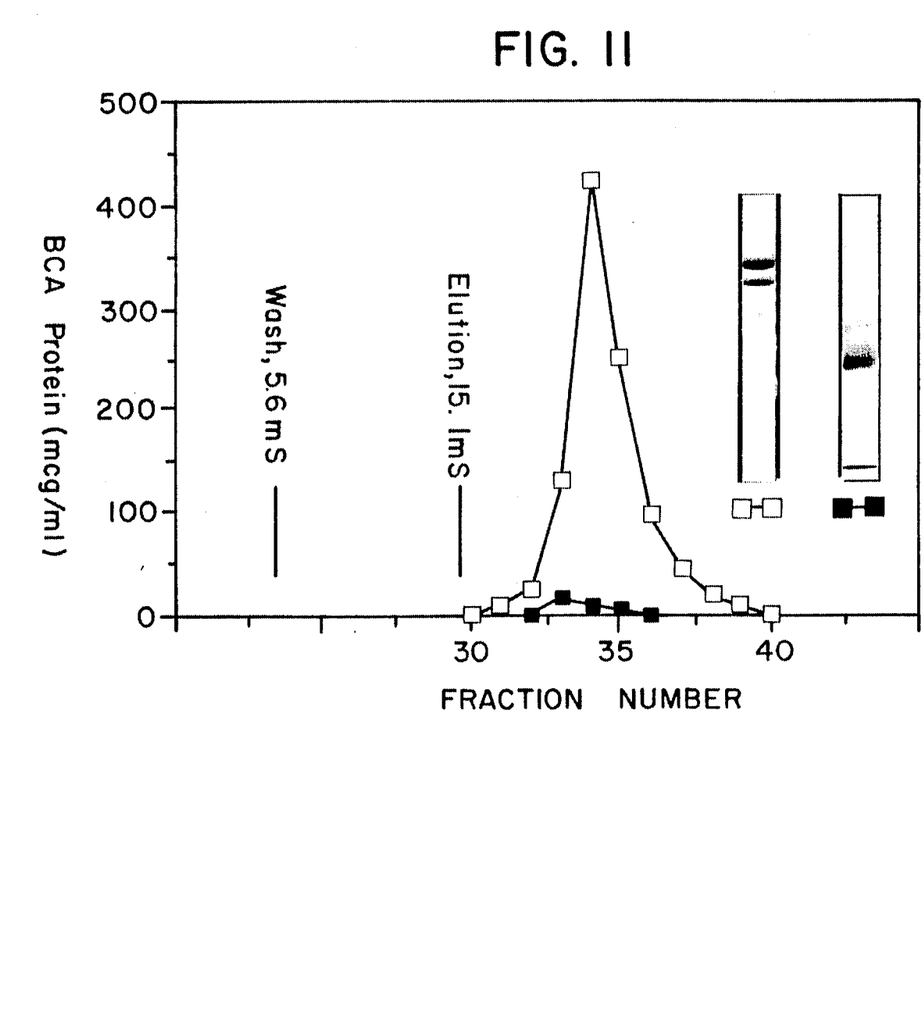
Figure 3:
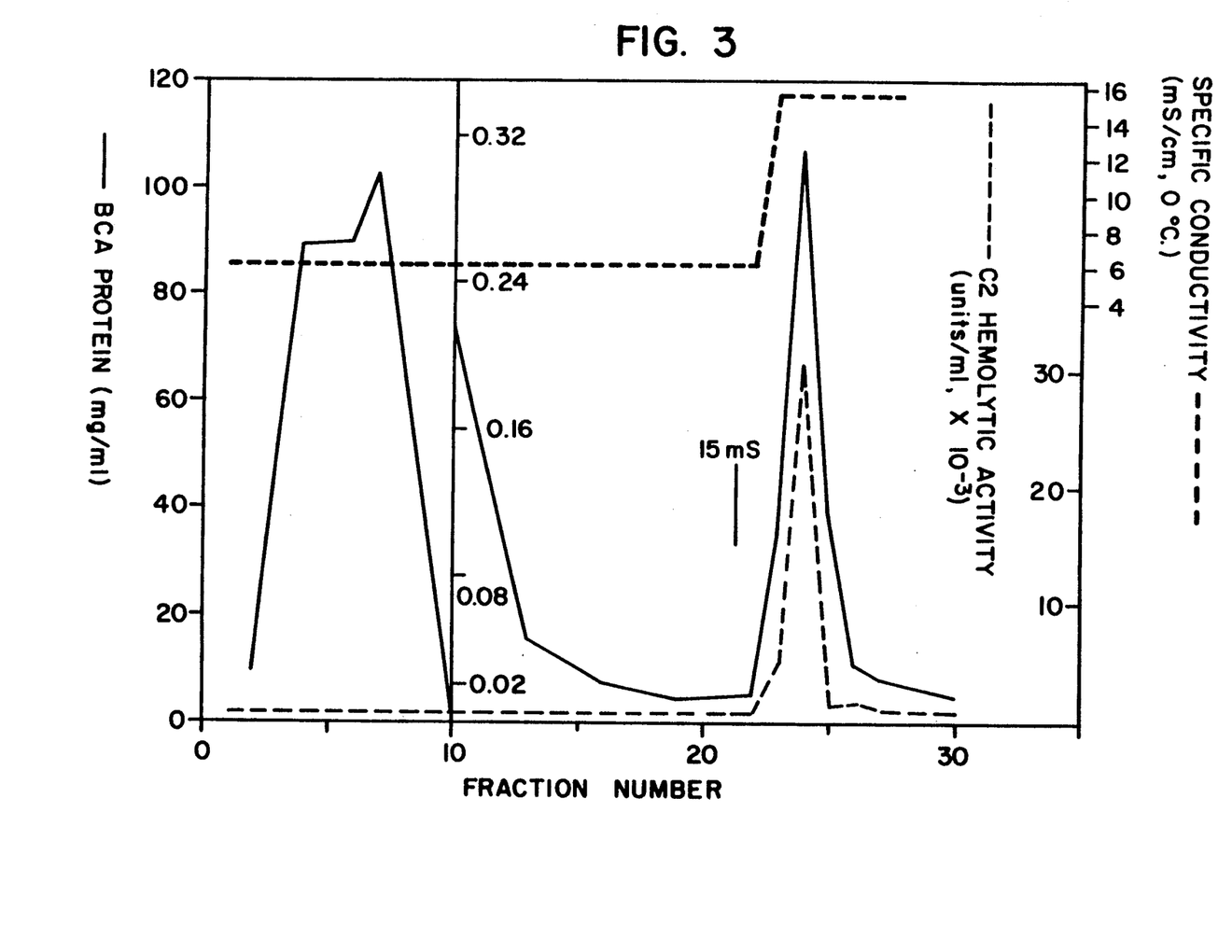
FIG. 3. Affinity chromatography of the 120 kDa and C2 protein from the PEG concentrate on iC4/C4b-Sepharose.

The efficiency and speed of the protein purification at the affinity chromatography step of the protocol appears to be important in maintaining the stability of the 120 kDa protein (FIG. 3). IEP analysis of the 120 kDa protein (FIG. 2) and functional testing of the C2 protein from the crude 7.6–21.4% PEG cut a few hours after preparation demonstrates rapid inactivation of both proteins.

FIG. 2 shows that the majority of 120 kDa protein was found in the 7.6–21.4% PEG fraction and showed a single, intense immunoprecipitate of slow alpha mobility (Well 4). Storage of this cut for two days (Well 7) or serum for eight days (Well 9) at 4° C. resulted in the conversion of the 120 kDa protein into at least two fragments having distinct antigenic determinants. Antigens in the remaining wells were: (1) fresh plasma; (2) 7.6% PEG precipitate; (3) 7.6% PEG supernatant; (5) 21.4% PEG supernatant; (6) and (8) serum ($-80°$ C.).

All troughs contained rabbit anti-120 kDa protein serum.

Figure 4:
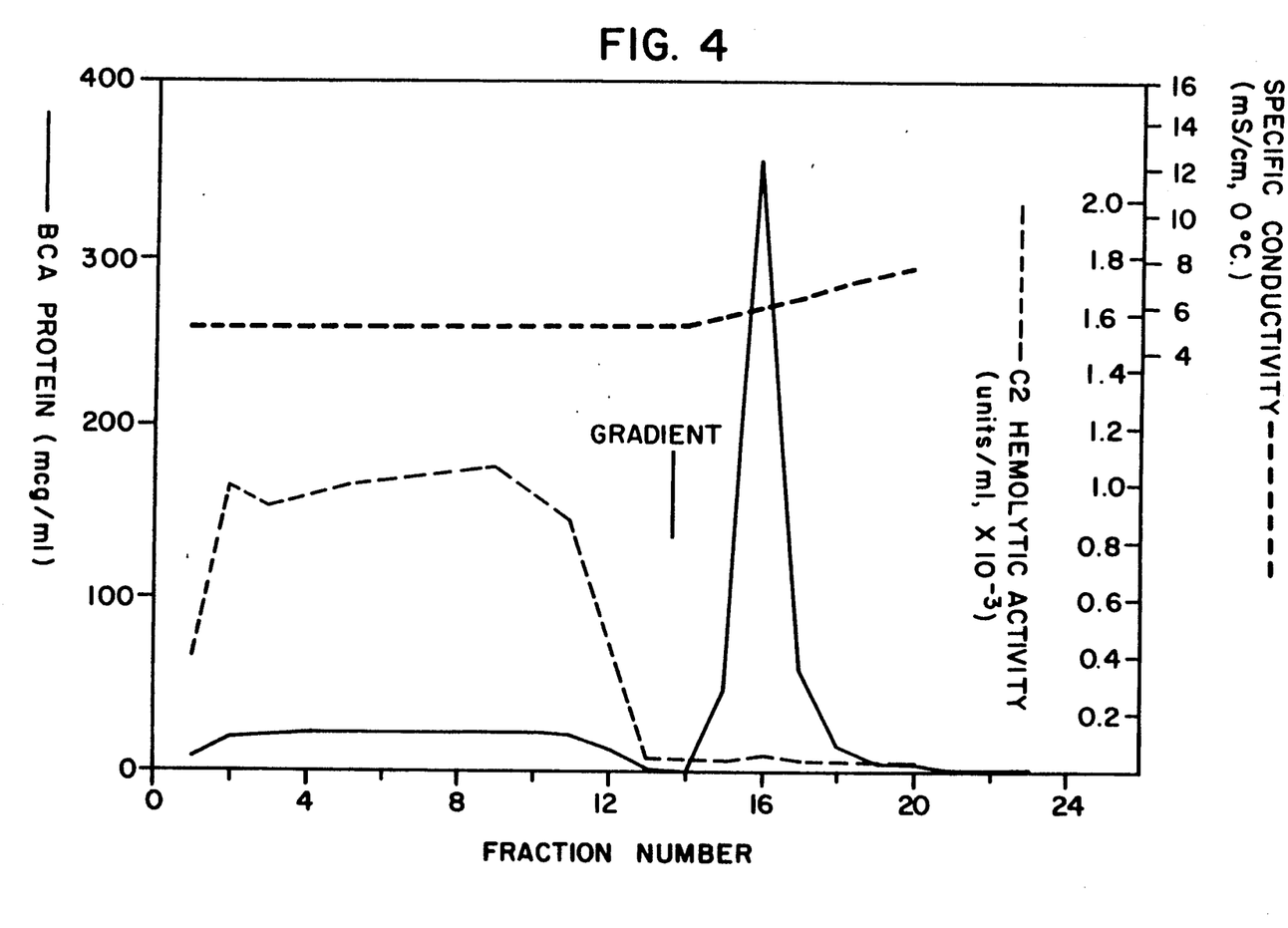
FIG. 4. DEAE-Sephacel chromatography utilized to effect separation of C2 from the co-isolating 120 kDa protein.

The 120 kDa protein and C2 are recovered together by elution with GVBS, 15 milliSiemens (mS). Because of their differing charge and purity, the co-isolated proteins can be completely separated from one another by gradient elution from DEAE-Sephacel (FIG. 4). The 120 kDa and C2 proteins which were pooled at 15 mS from the iC4/C4b-Sepharose column were diluted and applied at 5.6 mS to a column containing 4 ml of DEAE-Sephacel. Complete recovery of C2 was obtained in the drop-through and was fully resolved from the 120 kDa protein which eluted at the beginning of the linear salt gradient.

Both C2 and 120 kDa protein losses due to adsorption and aggregation in this procedure are reduced by including 0.005% gelatin in all buffers. All procedures are performed at 4° C. PEG fractionation steps are equilibrated for 1 hour, and centrifugation of PEG precipitated solutions is carried out at 350,000$\times$g-min in a Sorvall RC2B centrifuge. All stock buffers are Millipore-filtered prior to dilution and use, and the conductivity of working buffers is measured at 0° C. NPGB at a final concentration of 25 $\mu$M is added to all working buffers prior to their use.

Buffers

The following buffers were used for the purification of the C2 and 120 kDa proteins: a 10 times concentrated stock of sodium Veronal, pH 7.35, prepared at 50 mM and containing 0.05% gelatin (GVB, 10$\times$); GVB, pH 7.35, diluted to 5 mM Veronal and 0.005% gelatin, =0.5 mS; GVB, pH 7.35, containing 2 mM MgCl$_2$ (GVBM, $\mu$=0.5 mS); GVB containing 90 mM NaCl (GVBS, M=5.6 mS); GVBS, $\mu$=5.6 mS, containing 2 mM MgCl$_2$ (GVBSM, $\mu$=5.6 mS); GVB containing 275 mM NaCl (GVBS, $\mu$=15.2 mS); GVB containing 1M NaCl (GVBS, $\mu$=48 mS)

Selection of inhibitor treated plasma

A variety of combinations of anti-coagulants and protease inhibitors were tested for optimal recovery of C2 activity in plasma or serum. Optimal yield was obtained using EDTA and NPGB at concentrations of 10 mM and 25 $\mu$M, respectively. Later preparations also included 50 $\mu$g/ml SBTI.

For the purification protocol, fresh plasma was obtained by collection of whole blood into a syringe containing stock anti-coagulant solution to yield a 5% dilution of the blood. Approximately 240 ml of anticoagulated blood was collected to recover 100–135 ml of EDTA/NPGB/SBTI plasma.

2. Enrichment of 120 kDa protein by PEG precipitation

Plasma fractionation was optimized for the recovery of C2 activity. Using this protocol, C2 distribution and yield was determined to parallel that for the 120 kDa protein through the PEG fractionation step. Treatment of NPGB/EDTA plasma with 7.6% (wt/vol) PEG permitted recovery of about 8.2 g of protein in the supernatant. This protein comprised the majority of the 120 kDa protein, as well as all of the C2 functional activity.

When the 7.6% PEG supernatant was brought to 21.6% PEG, an additional 1.8 g (22%) of supernatant protein was recovered. Optimal C2 yield and specific activity were obtained from the solubilized 7.6 to 21.4% PEG plasma precipitate.

The PEG plasma precipitate was solubilized in 20–30 ml of GVBM, $\mu$=5.6 mS with NPGB. Qualitative analysis of the distribution and mobility of the 120 kDa protein in the precipitate was assessed by IEP as shown in FIG. 2. The IEP was developed with a monospecific polyclonal rabbit antiserum prepared with pure 120 kDa protein. The majority of the 120 kDa protein was concentrated in the 7.6-21.4% PEG cut and showed a single and intense immunoprecipitate of slow alpha mobility identical to that observed in fresh serum (FIG. 2, wells 6 and 8). Only moderate reactivity was observed in the 7.6% PEG solubilized precipitate and little reactivity was found in the 21.4% supernatant. Thus, treatment of the NPGB/EDTA plasma with PEG successfully concentrated the 120 kDa antigen.

The importance of a rapid purification scheme to obtain a stable preparation of the 120 kDa protein should be reiterated here. As shown in FIG. 2, the 120 kDa protein concentrated in the 7.6-21.4% PEG cut was stored for two days at 4° C. and eight days at plasma concentration was cleaved into at least two fragments with distinct antigenic determinants (FIG. 2, wells 7 and 9, respectively). This conversion resulted in the generation of fragments with alpha and beta mobility that arose rapidly in the concentrated preparation and more slowly in the serum or plasma.

3. Affinity chromatography on iC4/C4b-Sepharose

An important aspect of the present protocol is the utilization of affinity chromatography of a resolubilized PEG plasma fraction on iC4/C4b-Sepharose followed by DEAE-Sephacel. One repetition of the affinity chromatography step for each component is required to obtain substantially pure protein products. A representative summary of the protein yield at each step of the protocol is shown in Table I.

Specifically, to a 1.5 cm diameter column containing 16 ml of iC4/C4b-Sepharose equilibrated in GVBSM, $\mu = 5.6$ mS, the 7.6-21.4% PEG cut containing the C2 and 120 kDa proteins was resolubilized in GVBSM, $\mu = 5.6$, and immediately applied to the iC4/C4b-Sepharose affinity column. Following application of the sample to the column at 30 ml/hr, the column was washed at the same flow rate with about 10 column volumes of equilibration buffer. The column was then eluted with about four column volumes of GVBS, $\mu = 15.2$ mS, at 60 ml/hr. Elution recovered less than 6 mg of protein, however, only 0.05% of the applied protein remained bound to the column (FIG. 3).

At this stage, co-isolating with C2 and comprising more than half the recovered protein is a single additional component, the 120 kDa protein.

The entire chromatographic profile was screened for protein by the BCA micro method and for C2 hemolytic activity. All protein and C2 functional activity was found to have eluted in the 15.2 mS buffer. This eluate was pooled and prepared for anion exchange chromatography on DEAE-Sephacel by dilution with GVB buffer, $\mu = 0.5$ mS, to yield 5.6 mS.

4. DEAE-Sephacel chromatography

The relatively "basic" C2 binds weakly to DEAE-Sephacel. The absence of the 120 kDa protein in preparations of C2 isolated in pilot experiments where DEAE-Sephacel was utilized suggested that the 120 kDa protein was relatively acidic. Thus, the C2/120 kDa protein pool prepared above was separated using DEAE-Sephacel.

In order to effect this separation, the protein pool was applied to a 1×5 cm column containing 4 ml of DEAE-Sephacel equilibrated with GVBS, $\mu = 5.6$ mS, at 12 ml/hr. Following application of the sample, the column was washed with two column volumes of equilibration buffer to complete elution of C2. The 120 kDa protein was then recovered from the column with a linear salt gradient of 40 ml to 15 mS, also at 12 ml/hr. The entire chromatographic profile was again assayed for protein and for C2 functional activity.

The results shown in FIG. 4 depict the separation at 5.6 mS of all C2 function in the drop through fractions prior to gradient elution of a single peak of co-isolating protein at 6-8 mS. The yield of 120 kDa protein at this step, which was about 1.9 mg or 4% of the antigen (Table I), was usually less than C2.

Following DEAE-Sephacel separation, two separate protein pools were prepared. One pool contained all the C2 protein identified in the drop-through, while the second pool (120 kDa protein), which was recovered from the gradient at 6- 7 mS, was identified by a single uniform peak of BCA protein lacking C2.

Both the C2 and 120 kDa protein pools were next rechromatographed on the iC4/C4b-Sepharose column to remove trace contaminants and to effect final protein purification as described below.

5. Final purification on iC4/C4b-Sepharose

Figure 5:
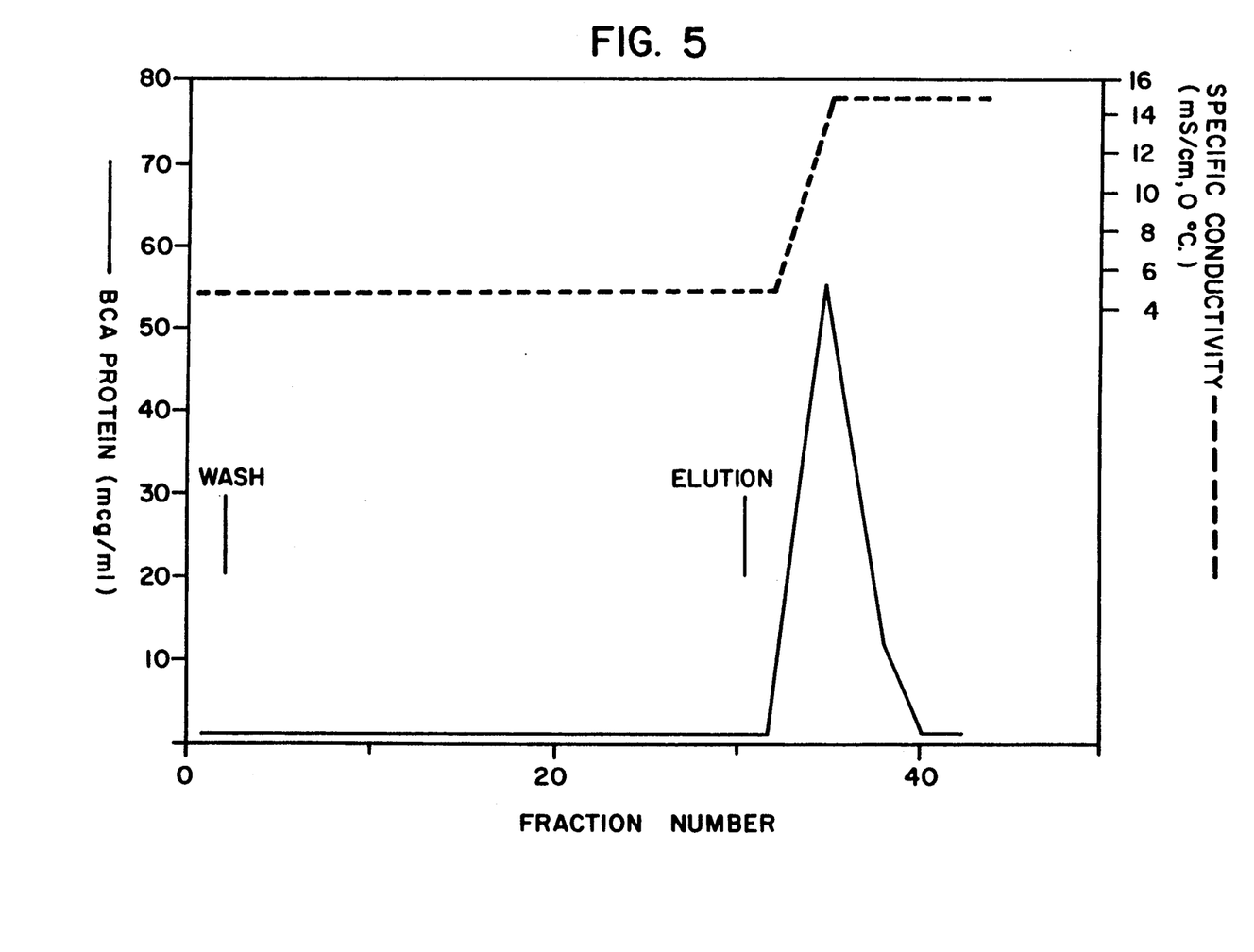
FIG. 5. Repeat affinity chromatography on iC4/C4b-Sepharose.

The last purification step for the 120 kDa protein entails a second adsorption at 5.6 mS to the iC4/C4b-Sepharose affinity column (FIG. 5). This step permits the removal of trace protein contaminations in the 120 kDa preparation including low levels of complement functional activity. It also permitted the determination of the requirement for C2 in the binding of the 120 kDa protein to the C4 ligand.

Thus, the iC4/C4b-Sepharose column was regenerated by treatment with 45 ml GVBS, $\mu = 48$ mS and equilibrated with GVBSM, $\mu = 5.6$ mS. Following dilution to 5.6 mS by the addition of GVBM, $\mu = 0.5$ mS, the 120 kDa protein was reapplied to the iC4/C4b-Sepharose column at 30 ml/hr. The column was washed with 120 ml of 5.6 mS buffer prior to step elution with GVBS at 15 mS as described for FIG. 3. Protein was determined using the micro BCA protein assay.

Generally, about 1.2 mg of purified co-isolating protein was obtained from 100-135 ml of plasma. For the preparation shown in Table I, 0.84 mg protein representing 0.69 mg antigen or 1.8% of 120 kDa was recovered. As described below, significantly more 120 kDa protein is present in plasma than that obtained by the method disclosed herein.

To determine the specificity of the 120 kDa protein for C4 fragments on the Sepharose matrix, the binding of the 120 kDa protein on iC4/C4b-Sepharose was compared with that on a control HSA-Sepharose column as depicted in FIG. 11. As shown in FIG. 11, NPGB/EDTA plasma was fractionated as before to obtain the 7.6-21.4% PEG cut containing the 120 kDa and the C2 proteins. The PEG fraction was divided and a portion was applied to an affinity column prepared with C4 fragments and a portion was applied to a control column prepared with HSA, both equilibrated to 5.6 mS in GVBSM. Each column was washed in the same buffer then eluted with GVBS, $\mu = 15$ mS, at 60 ml/hr. The collected fractions were assayed for BCA protein, 120 kDa antigen and C2 function.

As expected, over 5 mg of protein was recovered from the elution of the iC4/C4b-Sepharose column (□—□). Analysis of this protein profile showed direct correlation of protein with the 120 kDa protein antigen; the pool of protein containing all the 120 kDa antigen also contained all the C2 activity. SDS-PAGE of 30 μg of this pool showed the presence of both the 120 kDa and C2 proteins at the appropriate molecular weights and ratio. However, only 0.15 mg of protein was recovered from the pool.

No 120 kDa antigen or C2 activity was detected in the pool prepared from the HSA-Sepharose column (■—■). The SDS-PAGE of the recovered protein (shown in the inset for each profile) clearly demonstrated that the major protein constituent of this pool was HSA, which was most likely released from the Sepharose matrix. Excluding the HSA component, the level of protein bound to the HSA-Sepharose column was less than 0.05% of that bound to the iC4/C4b-Sepharose column.

From these results it is clear that the 120 kDa protein as well as the C2 protein require "C4" fragments on the Sepharose matrix as a site specific ligand.

F. Purity and relative molecular size a. SDS-PAGE

Figure 6:
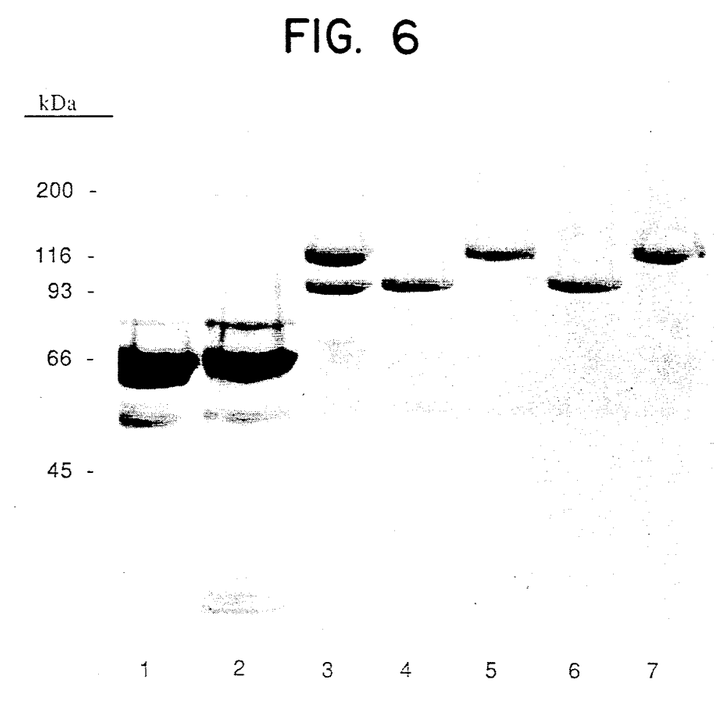
FIG. 6. SDS-PAGE analysis of the 120 kDa and the C2 proteins.

The purity and relative molecular size of the 120 kDa and C2 proteins isolated and purified as described above, were assessed by SDS-PAGE (8% gel) under reducing conditions with Coomassie Blue staining (FIG. 6). Under non-reducing conditions the molecular masses for both proteins remained unchanged.

The results in FIG. 6 are shown with respect to each step of the purification process: Lane 1, NPGB/EDTA plasma; Lane 2, 7.6–21.4% PEG cut; Lane 3, iC4/C4-b-Sepharose eluate; Lane 4, DEAE-Sephacel drop-through (C2); Lane 5, DEAE-Sephacel eluate (120 kDa protein); Lane 6, iC4/C4b-Sepharose second pass (C2); Lane 7, iC4/C4b-Sepharose second pass (120 KDa protein).

The iC4/C4b-Sepharose step allowed removal of 99.9% of the applied protein and resulted in recovery of two distinct components comprising almost all of the preparation (e.g. Lane 2 vs. Lane 3). The subsequent DEAE-Sephacel step cleanly separated the two proteins from each other (Lane 4: drop through containing C2 vs. Lane 5: eluate containing the co-isolating protein).

b. Functional purity—autoradiographic analysis

Functional complement assays sensitive to contamination levels well below that detectable by SDS-PAGE and autoradiographic analytic techniques were performed on the DEAE-Sephacel 120 kDa isolate. When assayed at 440 µg/ml, some trace level of functional contamination is apparent for a few complement components at this stage of purification (Table II); these are most likely removed following the last step of purification on iC4/C4b-Sepharose.

c. Radioiodination

For binding studies, and to further assess protein purity, both the C2 and the 120 kDa proteins were labeled with $^{125}$I by both N-chloro-benzenesulfonamide (Iodobead) and Bolton-Hunter reagent. $^{125}$I incorporation was identically ten times greater by the former method than by Bolton-Hunter, in which both the 120 kDa and C2 proteins were labeled to $3 \times 10^5$ cpm/µg. As expected, $^{125}$I-C2 labeled at tyrosine groups at $3 \times 10^6$ cpm/µg did not retain functional activity, while use of Bolton-Hunter reagent to label free amino groups preserved almost all lytic function.

Figure 7:
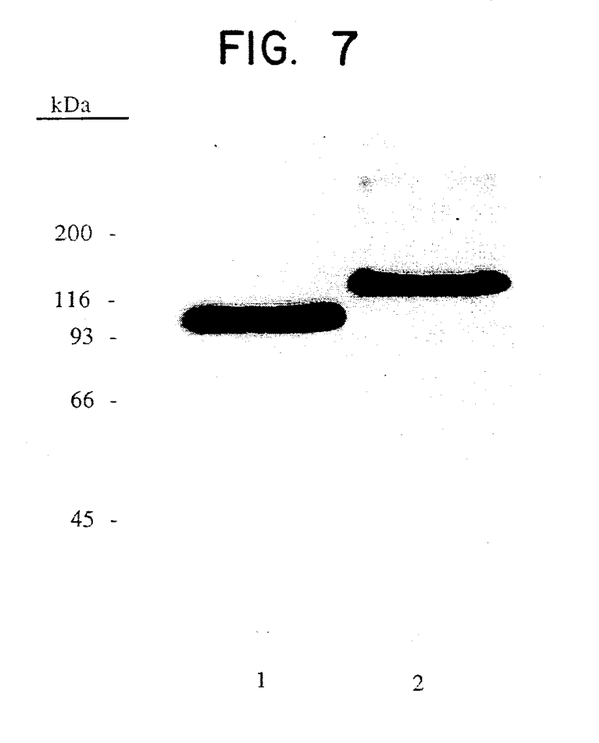
FIG. 7. SDS-PAGE autoradiographic analysis of $^{125}$I-120 kDa protein and $^{125}$I-C2.

Both the 120 kDa and the C2 proteins radioiodinated at amino functions with Bolton-Hunter reagent. Each protein radioiodinated to the same specific radioactivity of $3 \times 10^5$ cpm/µg. (FIG. 7). In FIG. 7, 116 ng of each labelled protein was applied to the gel and following electrophoresis and processing the proteins were visualized by exposing the dried gel to X-ray film for 4 hours at $-80°$ C. using Quanta III intensifying screens. Lane 1, C2; Lane 2, 120 kDa protein.

The biochemical purity of the proteins is evident from the lack of other well defined bands. The trailing weak smear seen in the 120 kDa protein lane was probably caused by aggregation of the parent molecule. Under non-reducing conditions the smear was exaggerated, even more so in the higher specific activity preparation (data not shown). Under more native conditions, the non-labeled protein showed none of this effect (FIG. 6).

d. Molecular size

Using SDS-PAGE analysis and by comparison to the molecular weight standards, the co-purifying proteins were assigned masses of 95 kDa for C2 and 120 kDa. Under non-reducing conditions, identical patterns of electrophoresis were obtained for both proteins. Repeat affinity chromatography resulted in the final purification of both the C2 (Lane 6) and the 120 kDa (Lane 7) proteins.

G. IEP analyses a. Production of antisera

Neither the anti-whole human serum (anti-WHS) nor any of twenty-three mono-specific test antisera immunoprecipitated with the 120 kDa protein at concentrations up to 600 µg/ml (FIG. 8—wherein the concentration for each antigen was: WHS, neat; C2, 400 µg/ml; and 120 kDa protein 440 °g/ml). The lack of reactivity of anti-WHS to the 120 kDa protein, as well as its failure to produce an antiserum by immunization of a goat with the 120 kDa protein suggests that this protein is a poor immunogen.

It should be noted, however, that an immunized rabbit did ultimately produce a monospecific antiserum to the 120 kDa protein which does not immunoprecipitate C2, and which reacts poorly with the antigen when compared, for example, to the results obtained with C2 and anti-C2.

Quantitative Mancini radial diffusion with rabbit antiserum, using purified 120 kDa protein for a standard, indicates the 120 kDa protein is present in serum at a concentration of about 300 µg/ml.

b. Effect of protease inhibitors on protein stability

Using IEP, various protease inhibitors and protein modifying agents, namely, E-amino caproic acid (ESCA, 50 mM); polybrene, 100 µg/ml; iodoacetamide, 20 mM; soybean trypsin inhibitor (SBTI, 50 µM); NPGB, 25 µM; EDTA, 10 mM, NaN$_3$, 15 mM (Sigma Chemical Co.); aprotinin, 1.5 µM, leupeptin, 1 µM and pepstatin A, 1 µM (Boehringer Mannheim Biochemicals, Indianapolis, Ind.) were tested for their ability to inhibit 120 kDa protein cleavage. The following is a listing of the inhibitors which slowed or prevented cleavage of the 120 kDa protein; they are recited in the order of their respective inhibiting activities: SBTI>aprotinin>NaN$_3$>leupeptin=pepstatin.

No cleavage of the 120 kDa protein was observed for periods of up to 21 days at 4° C. in solutions containing these inhibitors. SBTI prevented full cleavage for up to 67 days. Polybrene and EACA showed no effect, while iodoacetamide significantly accelerated cleavage of 120 kDa protein in serum.

c. Time-course of 120 kDa protein cleavage

Figure 10:
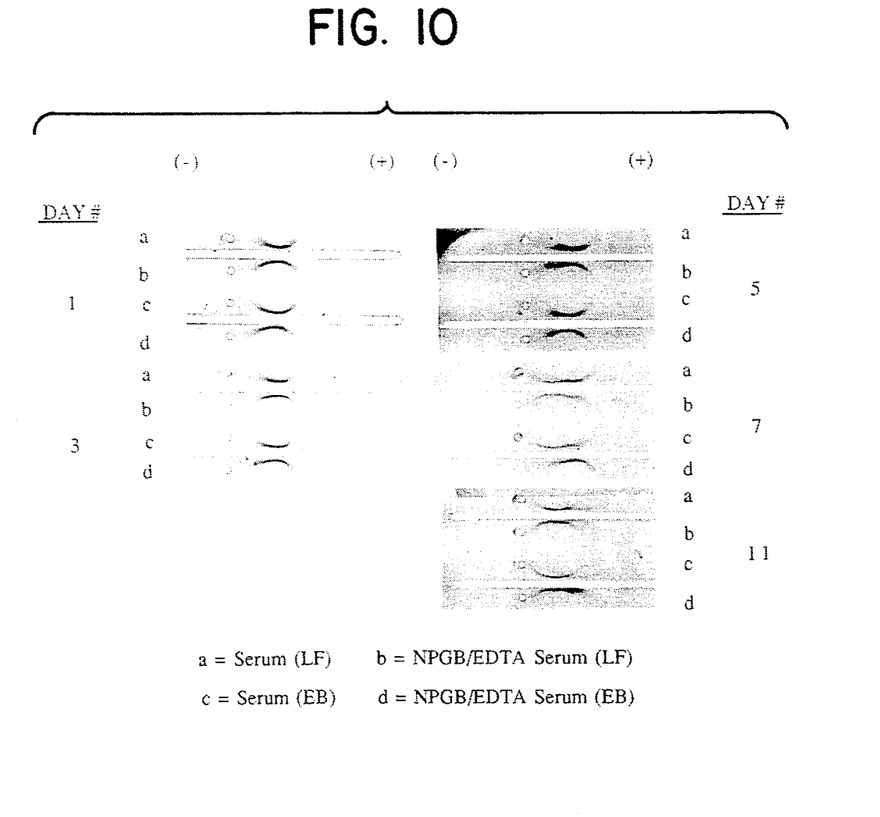
FIG. 10. IEP analysis of the kinetics of conversion of the 120 kDa protein.

The results of the IEP analysis show directly above demonstrate a time and concentration dependent conversion of the 120 kDa protein into at least two antigenically dissimilar components. This cleavage could arise from the action of a protease during the 120 kDa protein purification. Therefore, the kinetics of 120 kDa conversion in fresh serum and in NPGB/EDTA plasma (under preparation and storage conditions at 4° C.) was followed by IEP analyses over an eleven day period. The results of this study are shown in FIG. 10.

As shown, in both samples there was a slow, time dependent conversion (cleavage) of the 120 kDa protein into at least two distinct components at 4° C. Partial cleavage is seen by day five and is complete by day eleven with the formation of two components, one of alpha and one of beta mobility. Neither NPGB (25 μM) nor EDTA (10 mM) were effective in preventing fragmentation of the 120 kDa protein.

Western Blot analysis

Figure 9:
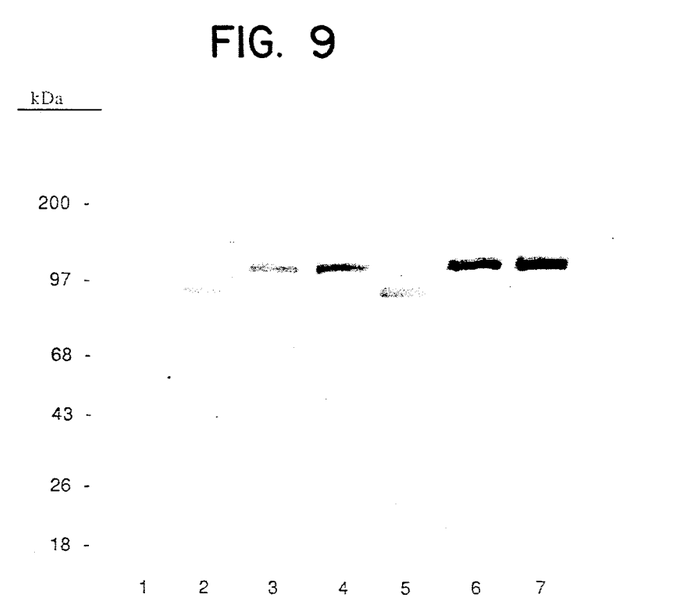
FIG. 9. SDS-PAGE protein blot analysis of the isolated 120 kDa and C2 protein.

As shown in FIG. 8, anti-serum to the 120 kDa protein does not immunoprecipitate C2. Similarly, antibody to C2 does not precipitate the 120 kDa protein. However, by sensitive Western bolt technique, anti-120 kDa protein antiserum was shown to react with the 120 kDa protein as expected, but also cross reacted with the C2 protein (FIG. 9). Similarly, polyclonal C2 anti-serum demonstrated weak cross reactivity to the 120 kDa protein.

In FIG. 9, 25 ng and 100 ng amounts of 120 kDa and C2 protein were electrophoresed on SDS-PAGE (8% gel), transferred to nitrocellulose and developed using mono-specific rabbit anti-120 kDa protein serum by standard methods. Reactivity to bovine serum albumin (far left lane) as a control at 1000 times the 120 kDa protein input, or, alternatively, in the absence of the first antibody (not shown) was negative. Lane 1, BSA; Lane 2, C2 (25 ng); Lanes 3 and 4, two preparations of 120 kDa protein (25 ng); Lane 5, C2 (100 ng); Lanes 6 and 7, two preparations of 120 kDa protein (100 ng).

I. Function of 120 kDa protein in complement pathway

The specific binding of the 120 kDa protein to iC4/C4b residues suggested that the functional role of the protein took place early in the classical complement pathway. Highly purified 120 kDa protein separated from C2 by DEAE-Sephacel chromatography was therefore used to assess the effect of 120 kDa protein incubation with EAC4b. The results of a series of experiments examining kinetic and dosage effects are shown in Table III.

Experiment 1 shows that with a 10 μg/ml pretreatment of EAC4b with 120 kDa protein, almost half the potential C1 fixing sites are inhibited. Inhibition was noted with both short (5 minute) or extended (30 minute) periods of incubation of the 120 kDa protein with EAC4b at 30° C. Subsequent experiments (i.e., 2, 3, 4) consistently demonstrated a dose-dependent inhibition of sites, with almost complete inhibition occurring at the highest dose of 120 kDa offered (about 160 μg/ml).

Experiment 5 shows that a single wash of EAC4b/120 kDa protein reduces the inhibitory effect of the 120 kDa protein. The fact that some inhibition remains suggests that the 120 kDa protein may bind to EAC4b and compete with C1 sterically to prevent C2 binding. This effect is fully reversible, however, since further washes eliminated the inhibition.

Binding of 120 kDa protein to the affinity matrix, independently of C2, is suggested by the fact that the protein can be rechromatographed on the affinity matrix in the absence of C2 (FIG. 5). The requirement of iC4/C4b for 120 kDa protein binding is clearly shown by the inability to purify 120 kDa protein with HSA-Sepharose (FIG. 11).

Absence of fragments on IEP, SDS-PAGE and Western Blot analysis (not shown) demonstrates that the purified 120 kDa protein is isolated from plasma in an intact form. However, the bulk of the 120 kDa antigen is not recovered by affinity isolation since repeated passes of the first drop-through produce diminishing recovery of the protein. Lack of stability of the 120 kDa protein may explain the inability to pass the column drop-through over the column a second time to significantly improve its yield. This concept is supported by the rapid cleavage of the 120 kDa protein which is shown by IEP analysis (FIG. 2) in the concentrated 7.6-21.4% PEG cut.

The purity of the final stage 120 kDa protein is evident from the results of physical (FIGS. 6 and 7), functional (Table II) and immunochemical (FIG. 8) tests. A similar molecular weight was obtained with reduced and unreduced proteins, thereby suggesting that the 120 kDa protein was not part of a higher molecular weight disulfide-linked complex. This finding does not exclude, however, non-covalent association in plasma.

IEP was used to assess the physical stability of the 120 kDa protein during its purification. Kinetic experiments utilizing IEP were also performed in serum and plasma at 4° C. to study the cleavage of the 120 kDa protein.

TABLE 1

Summary of 120 kDa protein purification

| STEP | VOLUME ml | BAC PROTEIN | | | RID Antigen | | |
|---|---|---|---|---|---|---|---|
| | | Conc. mg/ml | Total mg | Yield % | Conc. μg/ml | Total μg | Yield % |
| EDTA/NPGB SBTI plasma | 134 | 65.1 | 8,720 | 100.0 | 284 | 38100 | 100 |
| 7.6-21.4% PEG ppt | 34.5 | 54.5 | 1,880 | 21.6 | 1310 | 45100 | 118 |
| iC4/C4b-Sepharose#1 | 39.5 | 0.110 | 4.35 | 0.050 | 57.3 | 2260 | 5.9 |
| DEAE-Sephacel (C2 pool) | 9.5 | 0.176 | 1.670 | 0.019 | 0 | 0 | 0 |
| DEAE-Sephacel (120 kDa pool) | 26.5 | 0.070 | 1.860 | 0.021 | 55.8 | 1480 | 3.9 |
| iC4/C4b-Sepharose#2 (120 kDa pool) | 9.5 | 0.088 | 0.840 | 0.010 | 72.2 | 686 | 1.8 |

TABLE II

Functional purity of 120 kDa protein following DEAE-Sephacel chromatography

| COMPONENT ASSAYED | TITRE IN 120 kDa PROTEIN (units/ml) | TITRE IN HUMAN SERUM (units/ml) |
|---|---|---|
| C1 | <1 | 70,000 |
| C2 | <1 | 2,000 |
| C3 | 70 | 81,000 |
| C4 | 2 | 71,000 |
| C5 | 40 | 167,000 |
| C6 | 230 | 204,000 |
| C7 | 5 | 100,000 |
| C8 | 26 | 151,000 |
| C9 | 90 | 85,000 |
| C1 INH | 4 | 270,000 |
| 120 KD | 440 µg/ml | 300 µg/ml* |

*The concentration of 120 kDa protein was determined by Mancini radial immunodiffusion.

TABLE III 120 kDa Protein pretreatment of EAC4b: % inhibition of C1 site formation

| EXPT | 120 kDa PROTEIN (µg/ml) | TIME (min), 30° C. | | |
|---|---|---|---|---|
| | | 5 | 15 | 30 |
| | | % INHIBITION OF C1 SITES | | |
| 1.) | 10.3 | 44 | | 48 |
| 2.) | 1.4 | | 1.5 | |
| | 6.8 | | 14.9 | |
| | 25.4 | | 46.7 | |
| 3.) | 1.3 | | 0 | |
| | 8.8 | | 18.5 | |
| | 32.8 | | 53.8 | |
| 4.) | 39.6 | | 59.1 | |
| | 79.2 | | 76.5 | |
| | 158.4 | | 87.0 | |
| 5.)* | 1.8 | | 5.5 | |
| | 8.8 | | 16.1 | |
| | 32.8 | | 28.6 | |

*120 kDa-treated EAC4b washed prior to C1 addition.

We claim:

1. An essentially pure, single chain plasma glycoprotein having an approximate molecular mass of 120 kDa comprising the N-terminal amino acid sequence $(NH_2)$-EKNGIDIYSLTVD and the C-terminal amino acid sequence PPGVEISCWSVEL-(COOH).

2. The protein of claim 1 capable of being cleaved by activated Kallikrein into fragments of 85 and 35 kDa, said 85 kDa fragment capable of being further cleaved by activated Kallikrein into fragments of 60 and 25 kDa.

* * * * *